United States Patent [19]

Maurer et al.

[11] 4,315,008
[45] Feb. 9, 1982

[54] COMBATING PESTS WITH O-ETHYL-S-N-PROPYL-O-(1-SUBSTITUTED-PYRAZOL-4-YL)-(THIONO)-THIOLPHOSPHORIC ACID ESTERS

[75] Inventors: Fritz Maurer, Wuppertal; Ingeborg Hammann, Cologne; Bernhard Homeyer, Leverkusen, all of Fed. Rep. of Germany

[73] Assignee: Bayer Aktiengesellschaft, Leverkusen, Fed. Rep. of Germany

[21] Appl. No.: 95,725

[22] Filed: Nov. 19, 1979

[30] Foreign Application Priority Data

Dec. 16, 1978 [DE] Fed. Rep. of Germany ....... 2854389

[51] Int. Cl.³ .......................... A01N 57/16; C07F 9/65
[52] U.S. Cl. .................................. 424/200; 548/116; 548/358
[58] Field of Search .................. 548/116; 424/200

[56] References Cited

U.S. PATENT DOCUMENTS 4,163,052  7/1979  Hofer et al. ..................... 424/200

FOREIGN PATENT DOCUMENTS 184580   2/1956  Austria .
2603215  8/1977  Fed. Rep. of Germany .
2639258  3/1978  Fed. Rep. of Germany .

*Primary Examiner*—John M. Ford
*Assistant Examiner*—Natalia Harkaway
*Attorney, Agent, or Firm*—Sprung, Felfe, Horn, Lynch & Kramer

[57] ABSTRACT

O-Ethyl-S-n-propyl-O-(1-substituted-pyrazol-4-yl)-(thiono)-thiolphosphoric acid esters of the formula

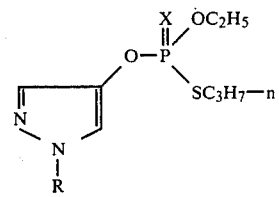

wherein
R is alkyl, cycloalkyl or phenyl, and
X is oxygen or sulphur, which possess arthropodicidal and nematicidal properties.

9 Claims, No Drawings

COMBATING PESTS WITH O-ETHYL-S-N-PROPYL-O-(1-SUBSTITUTED-PYRAZOL-4-YL)-(THIONO)-THIOLPHOSPHORIC ACID ESTERS

The present invention relates to and has for its objects the provision of particular new O-ethyl-S-n-propyl-O-(1-substituted-pyrazol-4-yl)-(thiono)-thiol-phosphoric acid esters which possess arthropodicidal and nematicidal properties, active compositions in the form of mixtures of such compounds with solid and liquid dispersible carrier vehicles, and methods for producing such compounds and for using such compounds in a new way especially for combating pests, e.g. insects, acarids and nematodes, with other and further objects becoming apparent from a study of the within specification and accompanying examples.

It is known that certain O-pyrazol-5-yl-O-ethyl-S-n-propyl-thionothiolphosphoric acid esters, for example O-(4-ethoxy-1-methyl-pyrazol-5-yl)- and O-(4-methylthio-1-methyl-pyrazol-5-yl)-O-ethyl-S-n-propyl-thionothiolphosphoric acid ester, have a pesticidal action (see DE-OS (German Published Specification) 2,603,215).

However, the action of these compounds is not always completely satisfactory, especially in the case of low concentrations of active compound and when small amounts are used.

The present invention now provides, as new compounds, the O-pyrazol-4-yl-O-ethyl-S-n-propyl-(thiono)thiol-phosphoric acid esters of the general formula

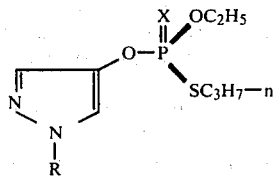

in which
R represents alkyl, cycloalkyl, or phenyl and
X represents oxygen or sulphur.
Preferably, in formula (I),
R represents straight-chain or branched alkyl with 1 to 5 carbon atoms, cycloalkyl with 3 to 8 carbon atoms or phenyl and
X represents oxygen or sulphur.

Surprisingly, the compounds of the formula (I) according to the invention display a considerably higher insecticidal, acaricidal and nematicidal action than known compounds of similar structure and of the same type of action.

The invention also provides a process for the preparation of a compound of the formula (I), in which a 4-hydroxy-pyrazole of the general formula

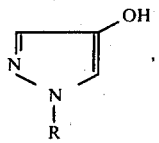

in which

R has the meaning indicated above, is reacted with an O-ethyl-S-n-propyl-(di)-thiophosphoric acid diester halide of the general formula

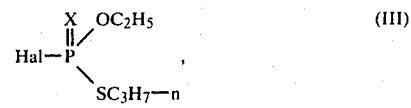

in which
X has the meaning indicated above and
Hal represents chlorine or bromine, especially chlorine, if appropriate in the presence of an acid acceptor and if appropriate using a diluent.

If, for example, 1-methyl-4-hydroxy-pyrazole and O-ethyl-S-n-propyl-thiolphosphoric acid diester chloride are used as starting materials, the reaction of these compounds can be outlined by the following equation:

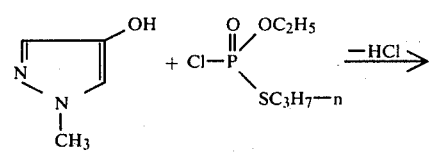

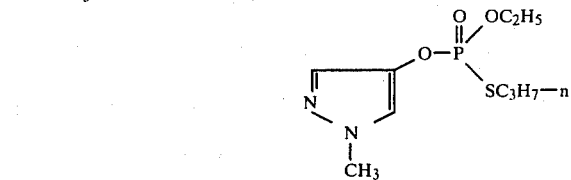

Formula (II) provides a definition of the 4-hydroxypyrazoles to be used as starting materials. Preferably, in this formula, R represents straight-chain or branched alkyl with 1 to 5 carbon atoms, cycloalkyl with 3 to 8 carbon atoms or phenyl.

Examples of the compounds (II) which may be mentioned are: 1-methyl-, 1-ethyl-, 1-n-propyl-, 1-iso-propyl-, 1-n-butyl-, 1-iso-butyl-, 1-sec.-butyl-, 1-tert.-butyl-, 1-n-pentyl-, 1-iso-pentyl-, 1-sec.-pentyl-, 1-tert.-pentyl-, 1-(1-ethyl)-propyl-, 1-cyclopropyl-, 1-cyclobutyl-, 1-cyclopentyl-, 1-cyclohexyl-, 1-cycloheptyl-, 1-cyclooctyl- and 1-phenyl-4-hydroxy-pyrazole.

4-Hydroxy-pyrazoles of the formula (II) are known (see Liebigs Ann. Chem. 313 (1900), 17). They are obtained, for example, by reacting known 4-methoxy-pyrazoles with hydrobromic acid. The 4-methoxy-pyrazoles are prepared in a known manner from hydrazines and 2-methoxy-3-dimethylamino-acrolein (see Archiv der Pharmazie 300 (1967), 704–708).

Examples which may be mentioned of the O-ethyl-S-n-propyl-(di)thiophosphoric acid diester halides (III) to be used as starting materials are: O-ethyl-S-n-propylthiolphosphoric acid diester chloride and O-ethyl-S-n-propyl-dithiophosphoric acid diester chloride. These compounds are already known.

The process for the preparation of the O-pyrazol-4-yl-O-ethyl-S-n-propyl-(thiono)thiolphosphoric acid esters according to the invention is preferably carried out using a suitable diluent (which term includes a solvent). Possible diluents are virtually any of the inert organic solvents. These include, as preferences, aliphatic and aromatic, optionally chlorinated hydrocarbons, such as benzine, benzene, toluene, xylene, methylene chloride, chloroform, carbon tetrachloride, chlorobenzene and o-dichlorobenzene; ethers, such as diethyl ether, dibutyl ether, tetrahydrofuran and dioxan; ketones, such as acetone, methyl ethyl ketone, methyl isopropyl ketone and methyl isobutyl ketone; and nitriles, such as acetonitrile and propionitrile.

Any of the customary acid-binding agents can be used as acid acceptors. Alkali metal carbonates and alcoholates, such as sodium carbonate and potassium carbonate and sodium methylate or ethylate and potassium methylate or ethylate, and furthermore aliphatic, aromatic or heterocyclic amines, for example triethylamine, trimethylamine, dimethylaniline, dimethylbenzylamine and pyridine, have proved particularly suitable.

The reaction temperature can be varied within a substantial range. The reaction is generally carried out at from 0° to 100° C., preferably at from 10° to 80° C. The process according to the invention is generally carried out under normal pressure.

The starting materials are usually employed in equimolar amounts for carrying out the process according to the invention. An excess of one or the other of the reactants brings no significant advantages. The reaction is generally carried out in a suitable diluent in the presence of an acid acceptor and the reaction mixture is stirred at the required temperature for several hours. An organic solvent, for example toluene, is then added and the organic phase is worked up in the customary manner by washing and drying and distilling off the solvent.

The new compounds are obtained in the form of oils, some of which cannot be distilled without decomposition, but are freed from the last volatile constituents by so-called "incipient distillation", that is to say by prolonged heating to moderately elevated temperatures under reduced pressure, and are purified in this manner. The refractive index is used for their characterization.

As already mentioned, the O-pyrazol-4-yl-O-ethyl-S-n-propyl-(thiono)thiol-phosphoric acid esters according to the invention are distinguished by an outstanding insecticidal, acaricidal and nematicidal activity.

They are active against plant pests and also against pests harmful to health and pests of stored products, and display only a low phytotoxicity. The compounds according to the invention can thus be successfully employed as agents for combating pests both in plant protection and in the hygiene field and in the protection of stored products.

The active compounds are well tolerated by plants, have a favorable level of toxicity to warm-blooded animals, and can be used for combating arthropod pests, especially insects and acarids, and nematode pests which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;*
from the class of the Diplopoda, for example *Blaniulus guttulatus;*
from the class of the Chilopoda, for example *Geophilus carpophagus* and Scutigera spec.;
from the class of the Symphyla, for example *Scutigerella immaculata;*
from the order of the Thysanura, for example *Lepisma saccharina;*
from the order of the Collembola, for example *Onychiurus armatus;*
from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;*
from the order of the Dermaptera, for example *Forficula auricularia;*
from the order of the Isoptera, for example Reticulitermes spp.;
from the order of the Anoplura, for example *Phylloxera vastatrix,* Pemphigus spp., *Pediculus humanus corporis,* Haematopinus spp. and Linognathus spp.;
from the order of the Mallophaga, for example Trichodectes spp. and Damalinea spp.;
from the order of the Thysanoptera, for example *Hercinothrips femoralis* and *Thrips tabaci;*
from the order of the Heteroptera, for example Eurygaster spp., *Dysdercus intermedius, Piesma quadrata, Cimex lectularius, Rhodnius prolixus* and Tritatoma spp.;
from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;
from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp.; *Bucculatrix thurberiella, Phyllocnistis citrella,* Agrotis spp.; Euxoa spp., Feltia spp., *Earias insulana,* Heliothis spp., *Laphygma exigua, Mamestra brassicae, Panolis flammea, Prodenia litura,* Spodoptera spp.; *Trichoplusia ni, Carpocapsa pomonella,* Pieris spp., Chio spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;*
from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;*
from the order of the Hymenoptera, for example Diprion spp., Hoplocampa spp., Lasius spp., *Monomorium pharaonis* and Vespa spp.;
from the order of the Diptera, for example Aedes spp., Anopheles spp., Culex spp., *Drosophila melanogaster,* Musca spp., Fannia spp., *Calliphora ery-*

*throcephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichodorus spp.

The active compounds can be converted into the customary formulations, such as solutions, emulsions, powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The present invention also provides an arthropodicidal or nematicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) or nematodes which comprises applying to the arthropods or nematodes, or to a habitat thereof, a compound of the present invention alone or in the form of a composition containing as active ingredient a compound of the present invention in admixture with a diluent or carrier.

The present invention further provides crops protected from damage by arthropods or nematodes by being grown in areas in which immediately prior to and/or during the time of the growing a compound of the present invention was applied alone or in admixture with a diluent or carrier.

It will be seen that the usual methods of providing a harvested crop may be improved by the present invention.

Preparation of the novel compounds is illustrated in the following example:

Example 1

(a) 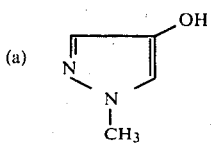

A solution of 11.2 g (0.1 mol) of 1-methyl-4-methoxypyrazole (for the preparation, see H. Plümpe and E. Schegk, Archiv der Pharmazie 300, 704–708 (1967)) in 70 ml of 48% strength hydrobromic acid was boiled under reflux for 18 hours and then evaporated to dryness in vacuo. The residue was dissolved in 50 ml of water and the solution was neutralized by adding sodium bicarbonate and then extracted 6 times with 50 ml of chloroform each time. The organic phases were dried over sodium sulphate and evaporated in vacuo. 4.1 g (42% of theory) of 1-methyl-4-hydroxy-pyrazole remained in the form of pale yellow crystals with a melting point of 71° C.

The following compounds of the formula

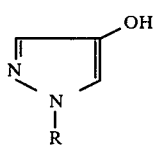 (II)

were prepared in an analogous manner:

| Intermediate | R | Yield (% of theory) | Physical data (melting point °C., refractive index) |
|---|---|---|---|
| b | $C_3H_7$—iso | 70 | 63 |
| c | $C_2H_5$ | 65 | $n_D^{20}$:1.5078 |
| d | ⌬ | 62 | 79 |
| e | $C_3H_7$—n | | |
| f | $C_4H_9$—n | 88 | $n_D^{20}$:1,5014 |
| g | $C_4H_9$—sec. | 51 | $n_D^{20}$:1,4991 |
| h | $C_4H_9$—iso | 79 | $n_D^{20}$:1,4961 |
| i | $C_4H_9$—tert. | | |
| j | $CH(C_2H_5)_2$ | | |
| k | ⟨H⟩ | | |

(b) 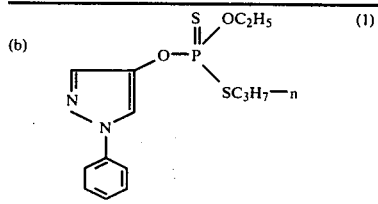 (I)

A mixture of 16 g (0.1 mol) of 1-phenyl-4-hydroxypyrazole (for the preparation, see Wolff and Fertig, Liebigs Ann. Chem. 313, 17 (1900)), 250 ml of acetonitrile, 15.2 g (0.11 mol) of potassium carbonate and 21.8 g (0.1 mol) of O-ethyl-S-n-propyl-thiono-thiol-phosphoric acid diester chloride was stirred at 45° C. for 6 hours. 400 ml of toluene were then added and the mixture was shaken twice with 300 ml of water each time. The organic phase was dried over sodium sulphate and evaporated in vacuo. The residue was subjected to incipient distillation at 80° C. 27.8 g (81% of theory) of O-ethyl-S-n-propyl-O-(1-phenyl-pyrazol-4-yl)-thionothiol-phosphoric acid ester were thus obtained in the form of a yellow oil with the refractive index $n_D^{22}$:1.5816.

The following compounds of the formula

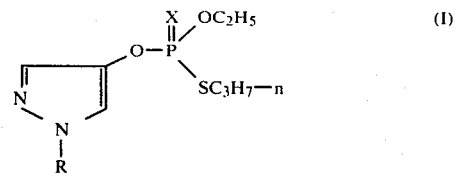 (I)

were prepared analogously:

| Compound No. | R | X | Yield (% of theory) | Refractive index: |
|---|---|---|---|---|
| 2 | $C_3H_7$—iso | S | 78 | $n_D^{21}$:1.5242 |
| 3 | $C_3H_7$—iso | O | 39 | $n_D^{20}$:1.4948 |
| 4 | $C_2H_5$ | S | 75 | $n_D^{20}$:1.5334 |
| 5 | ⌬ | S | 78 | $n_D^{23}$:1.5391 |
| 6 | ⌬ | O | | |
| 7 | $CH_3$ | S | 72 | $n_D^{24}$:1.5386 |
| 8 | $CH_3$ | O | | |
| 9 | $C_3H_7$—n | S | | |
| 10 | $C_3H_7$—n | O | | |
| 11 | $C_4H_9$—n | S | | |
| 12 | $C_4H_9$—sec. | S | 73 | $n_D^{23}$:1.5213 |
| 13 | $C_4H_9$—iso | S | | |
| 14 | $C_4H_9$—tert. | S | | |
| 15 | $CH(C_2H_5)_2$ | S | | |
| 16 | ⟨H⟩ | S | | |

The pesticidal activity of the compounds of this invention is illustrated by the following examples wherein the compounds according to the present invention are each identified by the number (given in brackets) from Example 1:

EXAMPLE 2

Plutella test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were treated by being dipped into a preparation of active compound and were infested with caterpillars of the diamond-back moth (*Plutella maculipennis*), as long as the leaves were still moist.

After the specified periods of time, the degree of destruction was determined as a percentage: 100% meant that all of the caterpillars were killed whereas 0% meant that none of the caterpillars were killed.

In this test, for example, the following compounds from preparative Example 1 showed a superior activity compared to the prior art: (2), (3), (4) and (12).

EXAMPLE 3

Myzus test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were treated by being dipped into the preparation of active compound of the desired concentration.

After the specified periods of time, the degree of destruction was determined as a percentage: 100% meant that all of the aphids were killed whereas 0% meant that none of the aphids were killed.

In this test, for example, the following compounds from preparative Example 1 showed a superior activity compared to the prior art: (1), (4), (7) and (12).

EXAMPLE 4

Tetranychus test (resistant)
Solvent 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were treated by being dipped into the preparation of the active compound.

After the specified periods of time, the degree of destruction was determined as a percentage: 100% meant that all of the spider mites were killed whereas 0% meant that none of the spider mites were killed.

In this test, for example, the following compounds from preparative Example 1 showed a superior activity compared to the prior art: (2), (3), (4), (7) and 12.

EXAMPLE 5

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil was decisive. The treated soil was filled into pots, lettuce was sown in and the potts were kept at a greenhouse temperature of 27 degrees C.

After 4 weeks, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

In this test, for example, the following compounds from preparative Example 1 showed a superior activity compared to the prior art: (1), (2), (3) and (4).

It will be appreciated that the instant specification and examples are set forth by way of illustration and not limitation, and that various modifications and changes may be made without departing from the spirit and scope of the present invention.

We claim:

1. An O-ethyl-S-n-propyl-O-(1-substituted-pyrazol-4-yl)-(thiono)-thiolphosphoric acid ester of the formula

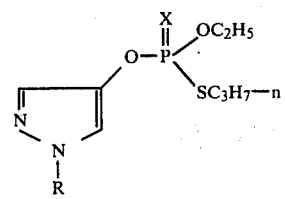

wherein
R is alkyl with 1 to 5 carbon atoms, cycloalkyl with 3 to 8 carbon atoms or phenyl, and
X is oxygen or sulphur.

2. A compound according to claim 1, wherein said compound is O-ethyl-S-n-propyl-O-(1-isopropyl-pyrazol-4-yl)-thionothiolphosphoric acid ester of the formula

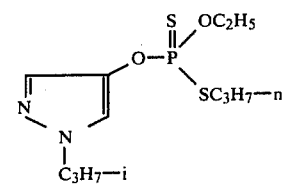

3. A compound according to claim 1, wherein said compound is O-ethyl-S-n-propyl-O-(1-isopropyl-pyrazol-4-yl)-thiolphosphoric acid ester of the formula

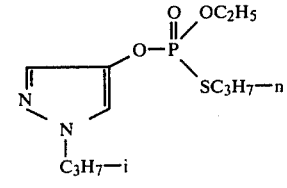

4. A compound according to claim 1, wherein said compound is O-ethyl-S-n-propyl-O-(1-ethyl-pyrazol-4-yl)-thiono-thiolphosphoric acid ester of the formula

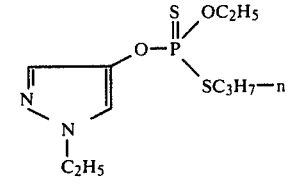

5. A compound according to claim 1, wherein said compound is O-ethyl-S-n-propyl-O-(1-methyl-pyrazol-4-yl)-thiono-thiolphosphoric acid ester of the formula

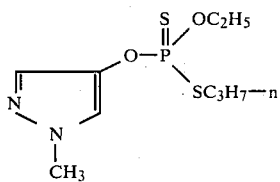

6. A compound according to claim 1, wherein said compound is O-ethyl-S-n-propyl-O-(1-sec.-butyl-pyrazol-4-yl)-thiono-thiolphosphoric acid ester of the formula

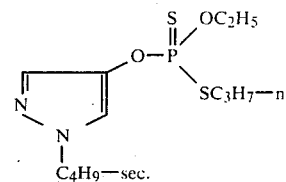

7. An arthropodicidal or nematicidal composition containing as active ingredient an arthropodicidally or nematicidally effective amount of a compound according to claim 1 in admixture with a diluent.

8. A method of combating arthropods or nematodes which comprises applying to the arthropods or nematodes, or to a habitat thereof, an arthropodicidally or nematicidally effective amount of a compound according to claim 1.

9. The method according to claim 8, wherein said compound is O-ethyl-S-n-propyl-O-(1-isopropyl-pyrazol-4-yl)-thiono-thiolphosphoric acid ester,
O-ethyl-S-n-propyl-O-(1-isopropyl-pyrazol-4-yl)-thiolphosphoric acid ester,
O-ethyl-S-n-propyl-O-(1-ethyl-pyrazol-4-yl)-thiono-thiolphosphoric acid ester,
O-ethyl-S-n-propyl-O-(1-methyl-pyrazol-4-yl)-thiono-thiolphosphoric acid ester or
O-ethyl-S-n-propyl-O-(1-sec.-butyl-pyrazol-4-yl)-thiono-thiolphosphoric acid ester.

* * * * *